United States Patent
Durling et al.

(10) Patent No.: US 9,439,748 B2
(45) Date of Patent: Sep. 13, 2016

(54) PESSARY DEVICE

(71) Applicant: The Procter & Gamble Company, Cincinnati, OH (US)

(72) Inventors: Evan Joseph Durling, West Chester, OH (US); Robert Clark Avery, Jr., Mason, OH (US); Kevin Charles Strong, Loveland, OH (US); Hinrich Knuth, Mason, OH (US); Daniel Raymond Wiegele, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 523 days.

(21) Appl. No.: 13/648,702

(22) Filed: Oct. 10, 2012

(65) Prior Publication Data

US 2014/0100416 A1    Apr. 10, 2014

(51) Int. Cl.
| | | |
|---|---|---|
| *A61F 6/08* | (2006.01) | |
| *A61F 2/00* | (2006.01) | |
| A61F 6/06 | (2006.01) | |
| A61F 6/12 | (2006.01) | |

(52) U.S. Cl.
CPC .............. *A61F 2/005* (2013.01); *A61F 6/08* (2013.01); *A61F 2/0004* (2013.01); *A61F 6/06* (2013.01); *A61F 6/12* (2013.01)

(58) Field of Classification Search
CPC ............. A61F 6/06; A61F 6/08; A61F 6/12; A61F 2/0004; A61F 2/0031; A61F 2/005
USPC .................................. 128/830–841; 600/29
See application file for complete search history.

(56) References Cited

U.S. PATENT DOCUMENTS

| | | | |
|---|---|---|---|
| 5,102,253 A | 4/1992 | Pugliesi-Conti et al. | |
| 6,676,594 B1 * | 1/2004 | Zunker | A61F 2/005 600/29 |
| 7,263,999 B2 * | 9/2007 | Kaseki | A61F 6/08 128/830 |
| 8,043,205 B2 | 10/2011 | Maclean | |
| 2007/0244352 A1 | 10/2007 | Ziv | |
| 2009/0266367 A1 * | 10/2009 | Ziv et al. | 128/834 |
| 2009/0283099 A1 * | 11/2009 | Harmanli | 128/834 |

\* cited by examiner

*Primary Examiner* — Keri J Nelson
(74) *Attorney, Agent, or Firm* — Andres E. Velarde

(57) ABSTRACT

A pessary device having a top, a base, a length, a longitudinal axis, and a hollow interior. The pessary device has a hollow interior containing a protuberance.

20 Claims, 6 Drawing Sheets

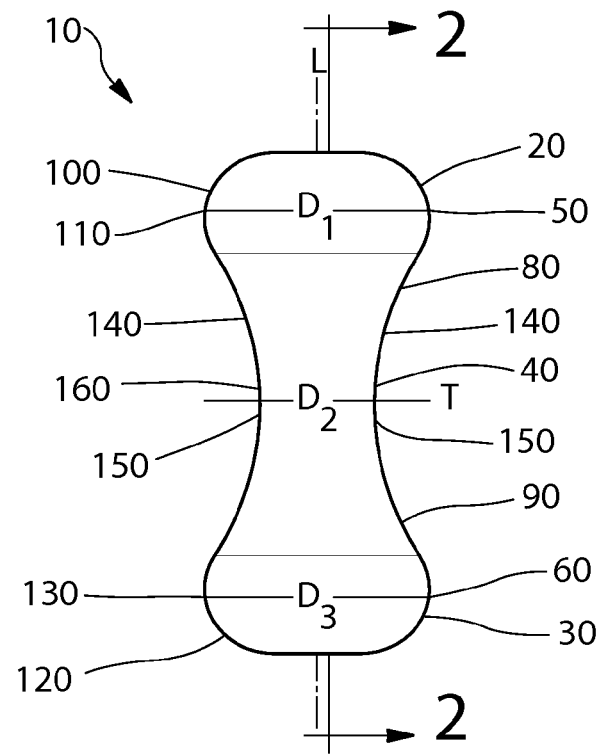
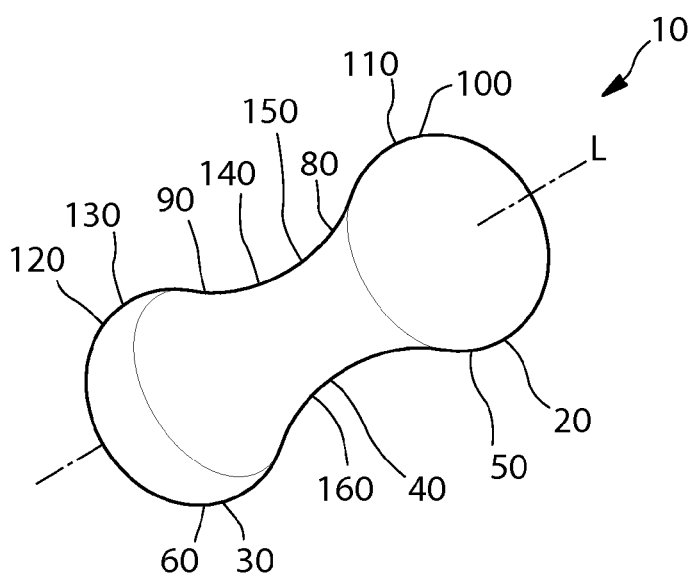
Fig. 1A
Fig. 1B

PESSARY DEVICE

FIELD OF INVENTION

This application relates to pessary devices for relief of female incontinence. More particularly, the present invention relates to pessary devices having improved configurations.

BACKGROUND OF THE INVENTION

Urinary incontinence, in which the ordinary bodily muscle functions fail to prevent unintended leakage of urine, is a common malady among women, particularly older women. It is estimated that up to 50% of women occasionally leak urine involuntarily, and that approximately 25% of women will seek medical advice at some point in order to deal with the problem. Stress incontinence, the most common type of urinary incontinence, refers to the involuntary loss of urine resulting from abdominal pressure rise, occurring during exercise, coughing, sneezing, laughing, etc. When stress incontinence occurs, it is usually the result of the abnormal descent of the urethra and bladder neck below the level of the pelvic floor. Many women wear sanitary napkins or diapers in order to deal with incontinence, and some women resort to surgical procedures.

Pessary devices are known to help relieve involuntary urination in a female. Such devices are designed for arrangement in the vagina for compressive action on and support of the bladder. Pessary devices inserted in the vaginal canal must be removed after use. A withdrawal member can be attached to the pessary device to ease with removal of the device. The withdrawal member should remain attached to the device. As such, there remains a need to attach the withdrawal member in a manner that secures the member and allows for ease of removal.

SUMMARY OF THE INVENTION

A pessary device that has a top, a base, a length, a longitudinal axis, and a hollow interior. The pessary device hollow interior has a protuberance that is used to anchor a withdrawal member.

A pessary device that has a top, a base, a length, a longitudinal axis, and a hollow interior. The hollow interior comprises a plurality of protuberances that provide structural support within the pessary device.

A pessary device that has a top, a base, a length, a longitudinal axis, and a hollow interior, wherein the hollow interior comprises two or more protuberances and a withdrawal member, wherein the two or more protuberances interlock by friction, and wherein the withdrawal member is held between the two or more protuberances.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 1A is a side view of a pessary device.
FIG. 1B is a perspective view of the pessary device of FIG. 1A.

DETAILED DESCRIPTION OF THE INVENTION

Figure 2:
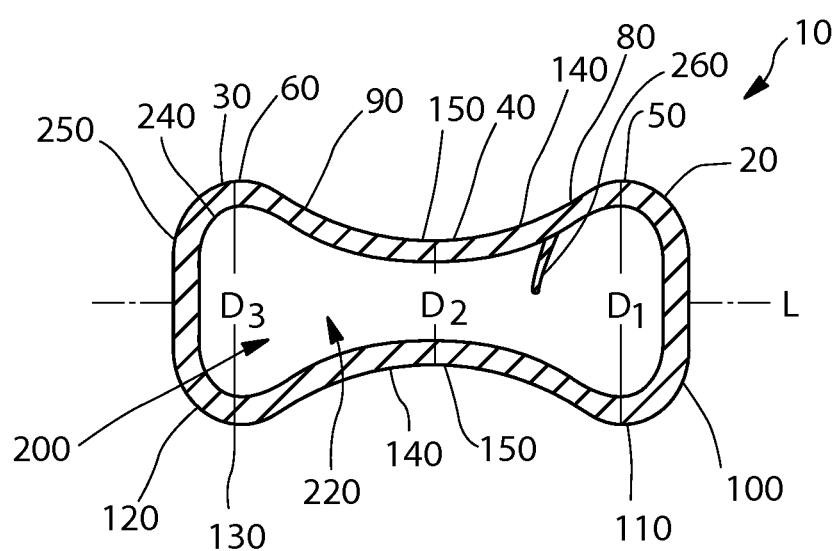
FIG. 2 is a cross-section view of the pessary device of FIG. 1A along 2-2.

The present invention is directed to pessary devices that are inserted into the female vagina to help control involuntary urinary incontinence. The pessary devices are small in size, and can provide improved comfort during use. The pessary device includes one or more protuberances contained in a hollow region. The pessary device can also have a withdrawal member. The withdrawal member can be joined to the one or more of protuberances. The protuberances can be integral or non-integral to the inner wall of the pessary device.

As used herein, "applicator" refers to a device or implement that facilitates the insertion of the pessary device into an external orifice of a mammal. Exemplary applicators include telescoping, tube and plunger, and compact applicators.

The term "joined" or "attached" as used herein, encompasses configurations in which a first element is directly secured to a second element by affixing the first element directly to the second element, configurations in which the first element is indirectly secured to the second element by affixing the first element to intermediate member(s) which in turn are affixed to the second element, and configurations in which first element is integral with second element, i.e., first element is essentially part of the second element.

As used herein, the term "non-expandable" refers to devices that do not expand prior to or during use, such as, for example, devices that do not increase in size or volume prior to or during use. For example, non-expandable devices have a diameter and/or volume that does not increase. In contrast, "expandable" as used herein, refers to devices that do increase in size or volume prior to or during use, such as, for example, devices that increase in diameter and/or length, absorb fluid into a fibrous or absorbent gelling material structure, or otherwise change from a first size or volume to a second size or volume, such as, for example, by inflation, absorption, mechanically, or by other means. Insubstantial changes to a non-expandable device as a result of any thermal expansion that could occur at body temperatures are not considered "expansion."

A "pessary device" or more particularly an "incontinence pessary device" as used herein refers to devices specifically designed, configured, and/or adapted for placement into a vagina in order to reduce the occurrence and/or severity of female urinary incontinence. A "pessary device" can include any type of substantially non-absorbent structure for the purpose of reducing urine leakage and/or supporting a prolapsed uterus and/or bladder. A pessary device does not include a menstrual tampon.

As used herein, the term "protuberances" refers to something that bulges out or projects from its surroundings.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

An exemplary pessary device 10 is shown in FIGS. 1A and 1B. The pessary device 10 includes an upper portion 20, a lower portion 30, a middle portion 40, a pressure region 50 of the upper portion 20, a pressure region 60 of the lower portion 30, a maximum diameter $D_1$, a minimum diameter $D_2$, a slope 80 extending from the upper portion 20 to the middle portion 40, a slope 90 from the middle portion 40 to the lower portion 30, a longitudinal axis (L) and a transverse axis (T). As shown in FIGS. 1A and 1B, the pessary device 10 can have a top 100 that includes a convex portion 110, a base 120 that includes a convex portion 130, and sides 140 that include concave portions 150. The pessary device can be symmetric about the longitudinal axis, including for example, wherein the base is circular and symmetric about the longitudinal axis. The pessary device can include a third diameter $D_3$ that is greater than minimum diameter $D_2$, and convex portion 110 can be aligned with maximum diameter $D_1$ to provide pressure region 50, and convex portion 130 can be aligned with maximum diameter $D_3$ to provide pressure region 60. In addition, concave portion 150 can be aligned with minimum diameter $D_2$ to form flexile region 160.

FIG. 2 shows a cross section of the pessary device 10 taken along line 2-2 of FIG. 1. The pessary device 10 includes an upper portion 20, a lower portion 30, a middle portion 40, a pressure region 50 of the upper portion 20, a pressure region 60 of the lower portion 30, a maximum diameter $D_1$, a minimum diameter $D_2$, a slope 80 extending from the upper portion 20 to the middle portion 40, a slope 90 from the middle portion 40 to the lower portion 30, and a longitudinal axis (L). As shown in FIG. 2, the pessary device 10 can have a top 100 that includes a convex portion 110, a base 120 that includes a convex portion 130, and sides 140 that include concave portions 150. As shown in FIG. 2, the pessary device 10 can have an interior 200 that is hollow. The pessary device has inner walls 240 that define interior 200 and hollow region 220. The hollow region 220 can have one or more protuberances 260 extending from the inner wall 240. In addition, the inner walls 240 can have the same or a similar profile as the outer walls 250.

Figure 3:
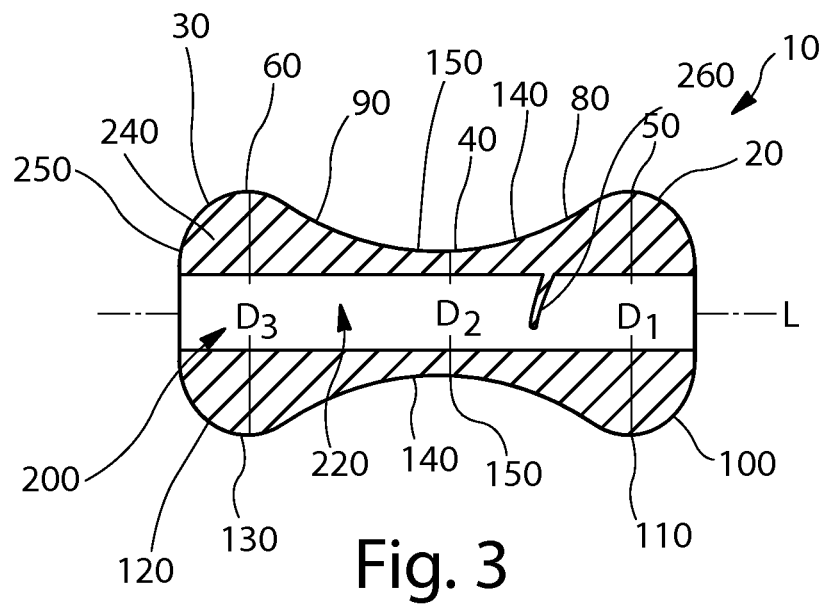
FIG. 3 is a cross-section view of a pessary device.

FIG. 3 shows a pessary device 10. The pessary device 10 includes an upper portion 20, a lower portion 30, a middle portion 40, a pressure region 50 of the upper portion 20, a pressure region 60 of the lower portion 30, a maximum diameter $D_1$, a minimum diameter $D_2$, a slope 80 extending from the upper portion 20 to the middle portion 40, a slope 90 from the middle portion 40 to the lower portion 30, and a longitudinal axis (L). As shown in FIG. 3, the pessary device 10 can have a top 100 that includes a convex portion 110, a base 120 that includes a convex portion 130, and sides 140 that include concave portions 150. As shown in FIG. 3, the pessary device 10 has an interior 200 that is hollow. The pessary device has inner walls 240 that define interior 200 and hollow region 220. The hollow region 220 can have a first profile defined by inner walls 240 and a different profile defined by outer walls 250, such as, for example, where the hollow region 220 is in the form of a tube. The hollow region 220 has a protuberance 260.

Figure 4:
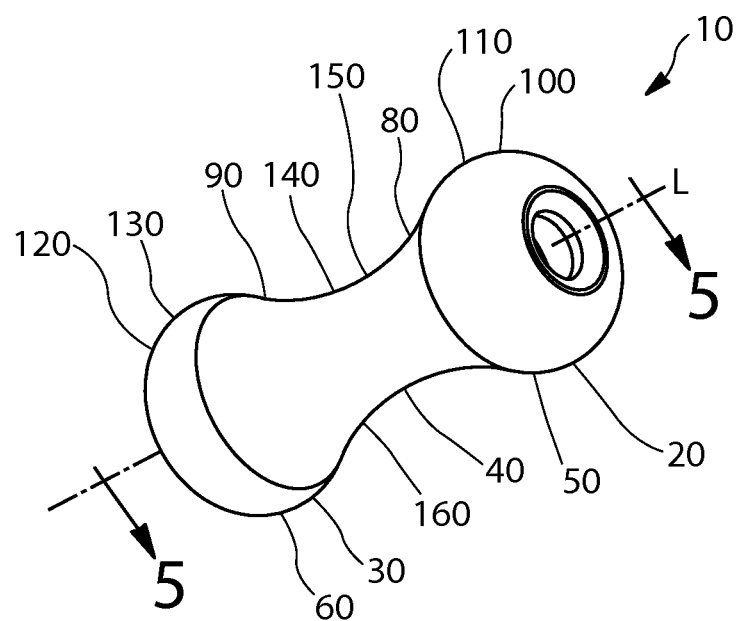
FIG. 4 is a perspective view of a pessary device.

FIG. 4 shows a pessary device 10. The pessary device 10 includes an upper portion 20, a lower portion 30, a middle portion 40, a pressure region 50 of the upper portion 20, a pressure region 60 of the lower portion 30, a slope 80 extending from the upper portion 20 to the middle portion 40, a slope 90 from the middle portion 40 to the lower portion 30, and a longitudinal axis (L). As shown in FIG. 4, the pessary device 10 can have a top 100 that includes a convex portion 110, a base 120 that includes a convex portion 130, and sides 140 that include concave portions 150. The pessary device can also have a flexile region 160. The pessary device 10 can have an interior 200 that is hollow. In addition, as shown in FIG. 4, the pessary device 10 can have an opening on one or more of top 100 and/or on base 120.

FIGS. 5A-I show multiple embodiments of pessary devices 10 taken along line 5-5 of FIG. 4. As shown in FIGS. 5A-I, the pessary device 10 can have outer wall 250 and an interior 200 defined by inner walls 240 that is hollow in region 220. The hollow region can contain protuberances 260 that can be integral or non-integral to the inner wall 240. The protuberances 260 can cross the longitudinal axis of the pessary device. The protuberances 260 can contact at the longitudinal axis or between the longitudinal axis and the inner wall. The protuberances 260 can interlock with each other by any suitable method, such as, for example, lock and key, hooking parts, ball and socket, and/or friction. The pessary device 10 can have a withdrawal member 310.

Figure 5A:
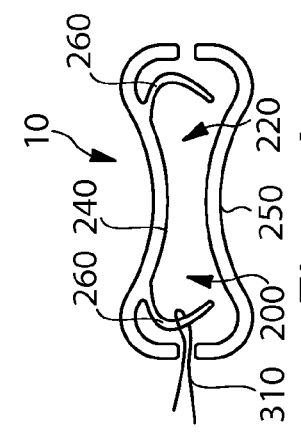
FIGS. 5A-I are embodiments of a cross section view of the pessary device of FIG. 4 along 5-5.

FIG. 5A shows a pessary device 10 containing an outer wall 250 and an interior 200 defined by inner walls 240 that is hollow in region 220. The hollow region 220 contains two protuberances 260 that are integral to the inner wall 240 of the pessary device 10. The protuberances 260 cross the longitudinal axis (L) inside the hollow region 220 of the pessary device 10. The withdrawal member 310 is anchored to a protuberance 260.

Figure 5B:
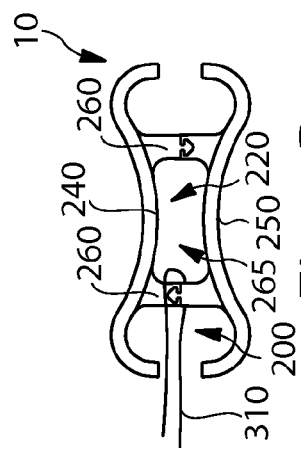

FIG. 5B shows a pessary device 10 containing an outer wall 250 and an interior 200 defined by inner walls 240 that is hollow in region 220. The hollow region 220 contains four protuberances 260 that are non-integral to the inner wall 240 of the pessary device 10. The protuberances 260 interlock by ball and socket inside the hollow region 220 of the pessary device 10. The protuberances 260 form an enclosed space 265. The withdrawal member 310 is attached to a protuberance 260.

Figure 5C:
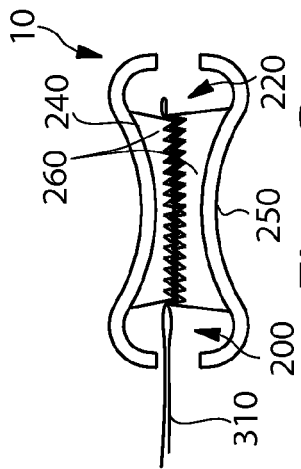

FIG. 5C shows a pessary device 10 containing an outer wall 250 and an interior 200 defined by inner walls 240 that is hollow in region 220. The hollow region 220 contains two protuberances 260 that are non-integral to the inner wall 240 of the pessary device 10. The protuberances 260 mirror each other and interlock by friction inside the hollow region 220 of the pessary device 10. The withdrawal member 310 is held between the two protuberances 260.

Figure 5D:
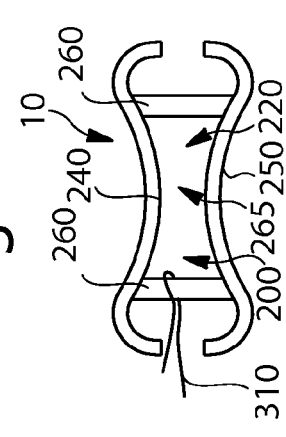

FIG. 5D shows a pessary device 10 containing an outer wall 250 and an interior 200 defined by inner walls 240 that is hollow in region 220. The hollow region 220 contains two protuberances 260 that are non-integral to the inner wall 240 of the pessary device 10. The protuberances 260 cross the longitudinal axis (L) and bridge the inner walls 240 of the hollow region 220 of the pessary device 10. The protuberances 260 form an enclosed space 265. The withdrawal member 310 is attached to a protuberance 260.

Figure 5E:
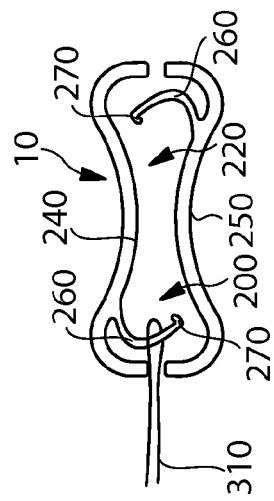

FIG. 5E shows a pessary device 10 containing an outer wall 250 and an interior 200 defined by inner walls 240 that is hollow in region 220. The hollow region 220 contains two protuberances 260 that are integral to the inner wall 240 of the pessary device 10. The protuberances 260 contain a hook 270 and cross the longitudinal axis (L) inside the hollow region 220 of the pessary device 10. The withdrawal member 310 is attached to a protuberance 260.

Figure 5F:
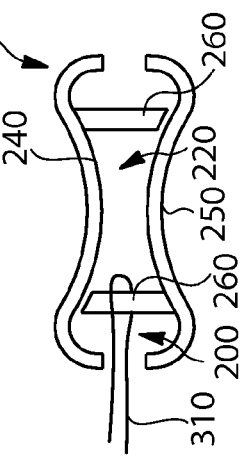

FIG. 5F shows a pessary device 10 containing an outer wall 250 and an interior 200 defined by inner walls 240 that is hollow in region 220. The hollow region 220 contains two protuberances 260 that are non-integral to the inner wall 240 of the pessary device 10. The protuberances 260 are straight and cross the longitudinal axis (L) inside the hollow region 220 of the pessary device 10. The withdrawal member 310 is attached to a protuberance 260.

Figure 5G:
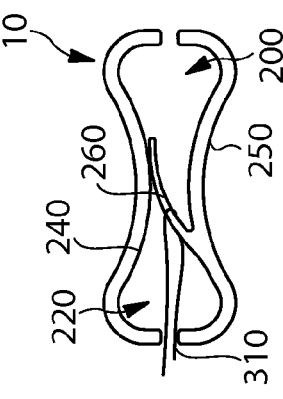

FIG. 5G shows a pessary device 10 containing an outer wall 250 and an interior 200 defined by inner walls 240 that is hollow in region 220. The hollow region 220 contains one protuberance 260 that is integral to the inner wall 240 of the pessary device 10. The protuberance 260 is curved, crosses the longitudinal axis (L) inside the hollow interior 220 of the pessary device 10, and contacts the opposing inner wall 240 of the pessary device 10. The withdrawal member 310 is attached to a protuberance 260.

Figure 5H:
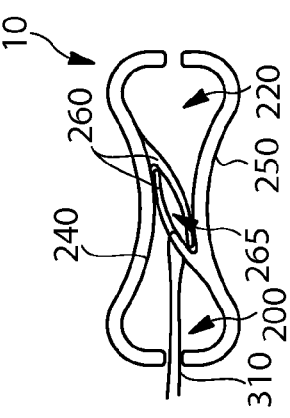

FIG. 5H shows a pessary device 10 containing an outer wall 250 and an interior 200 defined by inner walls 240 that is hollow in region 220. The hollow region 220 contains two protuberances 260 that are integral to the inner walls 240 of the pessary device 10. The protuberances 260 are curved, cross the longitudinal axis (L) inside the hollow interior 220 of the pessary device 10, and contact the opposing inner wall 240 of the pessary device 10. The protuberances 260 contact each other at the point where they extend from the inner wall 240. The protuberances 260 form an enclosed space 265. The withdrawal member 310 crosses through the enclosed space 265 between the two protuberances 260.

Figure 5I:
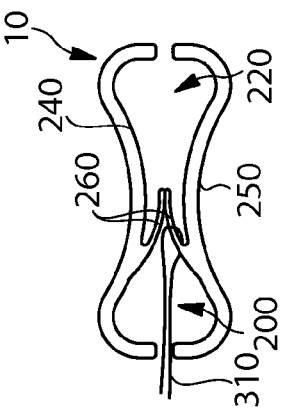

FIG. 5I shows a pessary device 10 containing an outer wall 250 and an interior 200 defined by inner walls 240 that is hollow in region 220. The hollow region 220 contains two protuberances 260 that are integral to the inner wall 240 of the pessary device 10. The protuberances 260 do not cross the longitudinal axis (L) inside the hollow interior 220 of the pessary device 10. The protuberances 260 meet at the longitudinal axis (L) of the pessary device 10 inside the hollow interior 220. The withdrawal member 310 is attached to a protuberance 260.

Figure 6:
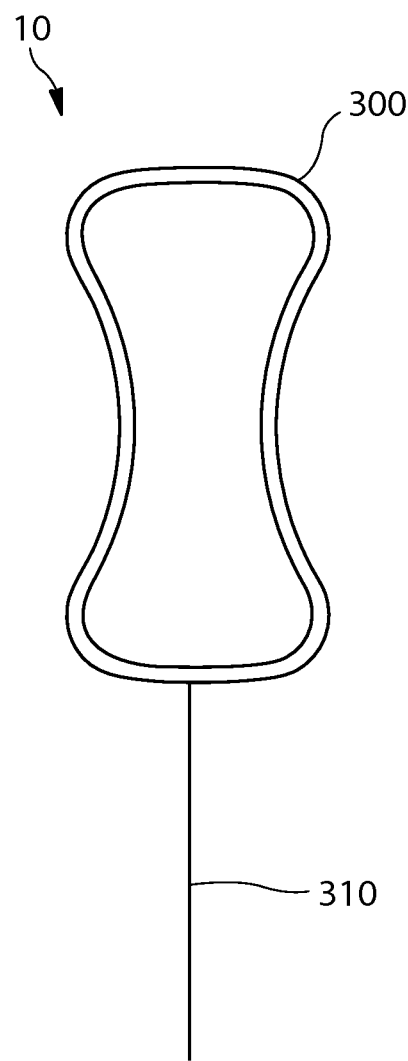
FIG. 6 is a side view of a pessary device.

The pessary device 10 can include an overwrap 300 and/or a withdrawal member 310, such as, for example, as shown in FIG. 6.

Figure 7:
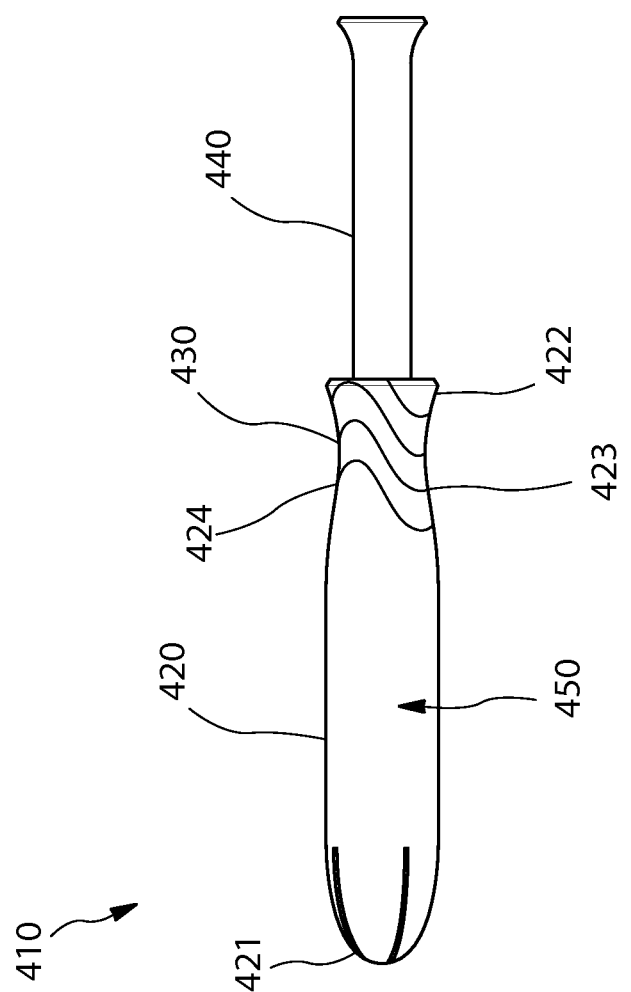
FIG. 7 is a side view of a pessary applicator, housing the pessary of FIG. 1.

The pessary device can be inserted in any suitable manner, such as, for example, using an applicator. FIG. 7 shows an applicator 410 that includes an insertion member 420 and a plunger 440. The insertion member 420 has an insertion end 421 and a withdrawal end 422 opposite the insertion end 421. The insertion member 420 also can include a barrel region 450 adapted to contain a pessary device, and a grip region 430 that can be an indentation region 424 provided opposite the insertion end 421, such as, e.g., proximal to the withdrawal end 422. The grip region 430 can include one or more grip elements 423.

The pessary device can be non-expandable. A portion or region of the pessary device can flex or be deformed, such as, for example, in the region having the minimum diameter, but the pessary device does not expand and returns to the original configuration after deformation. As such, the pessary device does not include any mechanical or other means that requires the user to change the size or shape of the pessary device during use, such as, for example, before or after insertion or prior to withdrawal. This provides for a pessary device that has a size upon withdrawal that is the same as the size during use, which can provide for improved comfort during use and withdrawal.

The pessary device can have a pressure region that has the maximum diameter of the pessary, such as, for example, at the base or at the top, that extends between the anterior vaginal wall and the posterior vaginal wall of a consumer to provide pressure on the urethra through the vaginal wall. In addition, the pessary device can have a second pressure region having an increased diameter as compared to the minimum diameter that can provide pressure on the urethra through the vaginal wall at a point apart from the first pressure region. The first pressure region and the second pressure region can be separated by any suitable distance, such as, for example, by at least about 5 mm, at least about 10 mm, at least about 15 mm, at least about 20 mm, at least about 25 mm, at least about 30 mm, at least about 35 mm, at least about 40 mm, at least about 45 mm, at least about 50 mm, or any other suitable distance.

The pessary device can have any suitable number of pressure regions, including for example, two pressure regions, such as, for example, four or fewer pressure regions, three or fewer pressure regions, two or fewer pressure regions, one pressure region, or any other suitable number of pressure regions.

The pressure region or regions can be any suitable shape, such as, for example, a convex shape that provides pressure to the vaginal wall, including, for example, a lobe. The pressure region or regions can have a substantially circular cross-section. The pessary device also can include a minimum diameter region that is a flexile region that can provide flexibility to the pessary device, such as, for example, by allowing bending or movement at the flexile region. The flexile region can be any suitable shape, such as, for example, concave, indented, or the like, and can have any suitable cross-section, such as, for example, a substantially circular cross-section. The pessary device can include a flexile region provided between two pressure regions.

The pessary device can provide resistance to force when placed inside a woman's vagina. For example, when the pessary device is inserted into the vagina, increases in abdominal pressure can act as a force on the pessary device through the vaginal wall. When the pessary device is disposed in the vagina lengthwise, that is, with the top of the pessary device positioned toward the cervix, the bottom of the pessary device positioned toward the introitus, and the length of the pessary device generally aligned with the length of the vagina, increases in abdominal pressure can act on the side of the pessary device, perpendicular to the length of the pessary device. Of course, increases in abdominal pressure can act on other regions of the pessary device, in addition or alternatively to acting on the side of the pessary device, including for example, when the pessary device is inserted into the vagina in an orientation other than lengthwise.

Despite its small size, the pessary device can provide a resistance to force of greater than about 10 psi, greater than about 15 psi, greater than about 20 psi, or greater than about 25 psi under about 2 newtons of force. For example, the pessary device can provide a resistance to force of greater than about 20 psi under about 2 newtons of force and greater than about 25 psi under about 3 newtons of force. The pessary device also can resist compression under pressure. For example, the pessary device can compress less than about 20% under about 2 newtons of force, less than about 15% under about 2 newtons of force, less than about 14% under about 2 newtons of force, less than about 13% under about 2 newtons of force, less than about 12% under about 2 newtons of force, less than about 11% under about 2 newtons of force, less than about 10% under about 2 newtons of force, less than about 9% under about 2 newtons of force, less than about 8% under about 2 newtons of force, less than about 7% under about 2 newtons of force, less than about 6% under about 2 newtons of force, less than about 5% under about 2 newtons of force, less than about 4% under about 2 newtons of force, less than about 3% under about 2 newtons of force, less than about 2% under about 2 newtons of force, or less than about 1% under about 2 newtons of force. For example, the pessary device can compress less than about 20% under about 2 newtons of force, less than about 15% under about 2 newtons of force, less than about 14% under about 2 newtons of force, less than about 13% under about 2 newtons of force, less than about 12% under about 2 newtons of force, less than about 11% under about 2 newtons of force, less than about 10% under about 2 newtons of force, less than about 9% under about 2 newtons of force, less than about 8% under about 2 newtons of force, less than about 7% under about 2 newtons of force, less than about 6% under about 2 newtons of force, less than about 5% under about 2 newtons of force, less than about 4% under about 2 newtons of force, less than about 3% under about 2 newtons of force, less than about 2% under about 2 newtons of force, or less than about 1% under about 2 newtons of force.

The pessary devices can provide a varied resistance to force along the longitudinal axis of the pessary device. For example, the pessary device can provide a resistance to force that is greater at the maximum diameter regions and smaller at the minimum diameter regions. In addition, the pessary device can compress differently along the longitudinal axis at different regions. For example, when force is applied to the side of the pessary, the minimum diameter region can compress at least about 5% more than the maximum diameter region under the same amount of pressure (for example, under about 200 g/m² of force), at least about 10% more than the maximum diameter region under the same amount of pressure, at least about 15% more than the maximum diameter region under the same amount of pressure, at least about 20% more than the maximum diameter region under the same amount of pressure, or at least 25% more than the maximum diameter region under the same amount of pressure. Any suitable amount of force can be applied, such as, for example, from about 200 g/m² of force to about 1500 g/m² of force, from about 200 g/m² of force to about 1400 g/m² of force, from about 300 g/m² of force to about 1200 g/m² of force, or from about 400 g/m² of force to about 800 g/m² of force.

The amount of resistance to force and the amount of compression under force provided by the pessary device as a whole or provided by the different regions of the pessary device can be measured in any suitable manner. For example, one suitable method employs a Universal Constant Rate Elongation/Tensile Tester with computer interface (MTS, Eden Prairie, Minn.). The method measures the force required to compress the pessary device resting on its side at 0.8 mm at a rate of 20 mm per min. For this method, the load probe tip is 5 mm in diameter and the tip is semi-spherical in shape. In addition, the resting fixture is a cylindrical steel plate 152 mm in diameter and 13 mm thick. The pessary device is placed on the steel table and the crosshead moves at 20 mm/min. When a force of 2 grams is exhibited on the pessary device, the crosshead automatically zeroes out and moves an additional 0.8 mm. The probe cycles back, and data is acquired at a rate of 100 Hz. This method measures the peak force in grams versus the amount of compression in mm. For pessary devices having varying diameters or widths, such as, for example, pessary devices having a maximum diameter or width and a minimum diameter or width, resistance to force at the different regions can be measured using this method. For example, for a pessary device as shown in FIGS. 1A and 1B, resistance to force at the maximum diameter regions $D_1$ and $D_3$ can be measured using a steel plate that is larger in size than the pessary device as the resting fixture. Resistance to force at the minimum diameter region $D_2$ can be measured using a single rod that contacts the minimum diameter region but not the maximum diameter regions.

Generally, the pressure region can be resistant such that the pressure region can provide pressure to the vaginal wall. The pressure region provides resistance under high stress pressures typical of the human vagina, such as, for example, by providing a maximum pressure to the urethra through the vaginal wall greater than about 5 psi, such as, for example, greater than about 10 psi, greater than about 15 psi, greater than about 20 psi, or greater than about 25 psi. In addition, the pressure region can provide a maximum urethral closure of greater than about 1.0 mm, such as, for example, greater than about 1.1 mm, greater than about 1.2 mm, greater than about 1.3 mm, greater than about 1.4 mm, such as, for example, greater than about 1.5 mm, greater than about 1.6 mm, greater than about 1.7 mm, greater than about 1.8 mm, or greater than about 1.9 mm. In addition, or alternatively, the pressure region can compress less than about 1 mm when measured under 0.5 psi when the force is applied from one side of the pressure region to the opposite side of the pressure region at the region of maximum diameter in the direction perpendicular to the longitudinal axis.

Maximum pressure to the urethra and maximum urethral closure can be measured using any suitable method, such as, for example, by using the computational model described in U.S. Patent Appln. No. 2007/0027667. For example, a computation model simulating the human internal pelvic environment can be used. In certain embodiments, thirteen nodes on the urethra in the simulation that are both on the back wall toward the vagina and in the middle of the body on the sagittal plane can be chosen. The points should be spread even along the length of the urethra with the first point at the bottom edge of the urethra and the last point at the bladder neck. Node vs. time vs. Von Mises stress should be obtained using a suitable software program, such as, for example, LS-Prepost, for all chosen nodes. The data columns are then matched to determine the y position vs. time vs. Von Mises stress. Generally, only the data that is at the simulation end point should be selected and y-position vs. Von Mises is then plotted.

The flexile region, on the other hand, is more flexible than and provides less resistance than the pressure region. Addition of the flexile region can allow the pessary device to flex in the longitudinal direction as well at the lateral direction. For example, the pessary device can compress more than about 1 cm when measured under 0.5 psi when the force is applied from the top to the base along the longitudinal axis. In addition, or alternatively, the flexile region can provide a bending region that facilitates the pessary device bending from side to side.

The pessary device can be a unitary construction. For example, the pessary device can include a continuous outer shell that defines the entire exterior surface of the pessary device. The outer shell can be smooth or textured. The outer shell can be permeable to fluid, such as, for example, by the inclusion of holes, pores, or other suitable openings. Alternatively, the outer shell can be impermeable to fluid such that fluid cannot enter the device. In addition, the pessary device can include an opening in the top and/or base. The pessary device can include an opening in the top and/or base and the outer shell is not permeable to fluid such that fluid cannot enter the device except through the opening in the top and/or base.

The pessary device can be constructed from two or more pieces. The two or more pieces can snap fit together to form a continuous outer shell that defines the entire exterior surface of the pessary device. The outer shell can be smooth or textured. The outer shell can be permeable to fluid, such as, for example, by the inclusion of holes, pores, or other suitable openings. Alternatively, the outer shell can be impermeable to fluid such that fluid cannot enter the device. In addition, the pessary device can include an opening in the top and/or base. The pessary device can include an opening in the top and/or base and the outer shell is not permeable to fluid such that fluid cannot enter the device except through the opening in the top and/or base.

Suitable pessary devices have a hollow interior. The pessary device can have an outer periphery defining a total area of the device and an inner periphery defining an open area of the device. The open area can be any suitable size, such as, for example, between about 5% to about 95% of the total area, such as, for example, from about 10% to about 90% of the total area, from about 15% to about 85% of the total area, or from about 20% to about 80% of the total area. In addition, the pessary device also can have a wall thickness that is suitable to maintain the pessary configuration. The wall thickness can be greater than about 1 mm, such as for example, about 2 mm, about 3 mm, about 4 mm, about 5 mm, or greater. The wall thickness can be constant or varied along the length of the pessary device and/or around the circumference of the pessary device.

The pessary device can have any suitable outer shape having a varied diameter along the longitudinal axis, such as, for example, a shape having a varied diameter that is symmetrical with respect to the longitudinal axis, such as, for example, a teardrop, an apple, a pear, an hourglass, a waisted cylinder, a figure-8 shape, a peanut shape, a heart-shape, a light bulb shape, a bottle shape, a vase shape, or any other suitable shape. In addition, the shape can have a varied diameter and can be symmetrical with respect to both the longitudinal and lateral axis, such as, for example, an hourglass, a waisted cylinder, a figure-8 shape, a peanut shape, or any other suitable shape. Alternatively, the pessary device can have an asymmetrical shape, such as, for example, a B-shape or a P-shape. The pessary device can be symmetrical at one region and asymmetrical at another region, such as, for example, where the pessary device has a symmetrical pressure region and an asymmetrical flexile region. Generally, the pessary device can have a varying diameter that can provide varying pressure along the user's urethra. For example, the pessary device can have a convex portion that can correspond to the pressure region. In addition, the pessary device can have a minimum diameter region that can be a concave region. The concave region can correspond to the flexile region.

The pessary device can be hourglass shaped. For example, as shown in FIG. 1, the pessary device can have upper and lower portions joined together by a waistline portion, with the upper and lower portions having diameters that are both greater than a diameter of the waistline portion such that the pessary device has a generally hourglass configuration. In this configuration, the upper portion of the pessary device can have a top and the lower portion of the pessary device can have a base, and the pessary device can have sloping upper and lower wall sections joining the top and the base with the waistline portion. In addition, the waistline portion can include the minimum diameter of the pessary device. The upper and lower portions can have generally coequal maximum diameters, or the upper and lower portions can have different maximum diameters, such as, for example, where the upper portion has a maximum diameter greater than the lower portion or where the lower portion has a maximum diameter greater than the upper portion.

Generally, the pessary device includes at least one maximum diameter and at least one minimum diameter, where the minimum diameter is smaller than the maximum diameter. The pessary device can include a first portion having a maximum diameter, a second portion having a maximum diameter, and a third portion that has a minimum diameter. The maximum diameter of the first portion and the maximum diameter of the second portion can be separated by a distance that is greater than about 10% of the length of the pessary device, such as, for example, by a distance greater than about 5 mm, greater than about 10 mm, greater than about 15 mm, greater than about 20 mm, greater than about 25 mm, greater than about 30 mm, greater than about 35 mm, greater than about 40 mm, greater than about 45 mm, or more. The pessary device can provide pressure at mid-urethra, the bladder neck, or both. In addition, the pessary device can provide higher pressure at the mid-urethra, the bladder neck, or both and provides lower pressure at the area between the mid-urethra and the bladder neck. For example, the pressure region can provide pressure at levels about 25% higher than the pressure provided by the flexile region, such as, for example, at levels about 30% higher, about 35% higher, about 40% higher, about 45% higher, about 50% higher, about 55% higher, about 60% higher, or more.

The pessary device can have a slope from the maximum diameter to the minimum diameter. Any suitable slope can be used, including for example, about 0.25 mm, about 0.5 mm, about 0.75 mm, about 1 mm, about 1.5 mm, about 2 mm, about 2.5 mm, about 3 mm, about 4 mm, about 5 mm, about 6 mm, about 7 mm, about 8 mm, or more, such as, for example, a slope from about 0.25 mm to about 5 mm, or a slope from about 0.5 mm to about 4 mm, or any other suitable range.

Suitable pessary devices are typically smaller in size than conventional pessary devices. For example, the pessary devices have a maximum diameter, a length, and/or a volume that is smaller or less than that of conventional pessary devices.

The pessary devices can have any suitable maximum diameter, such as, for example, a maximum diameter of less than 55 mm, such as, for example, less than 50 mm, less than 45 mm, less than 40 mm, less than 35 mm, less than 34 mm, less than 33 mm, less than 32 mm, less than 31 mm, less than 30 mm, less than 29 mm, less than 28 mm, less than 27 mm, less than 26 mm, less than 25 mm, less than 24 mm, less than 23 mm, less than 22 mm, less than 21 mm, less than 20 mm, less than 19 mm, less than 18 mm, less than 17 mm, less than 16 mm, less than 15 mm, less than 14 mm, less than 13 mm, less than 12 mm, less than 11 mm, or less than 10 mm, including, for example, a maximum diameter of from about 10 mm to about 35 mm, from about 10 mm to about 25 mm, from about 13 mm to about 25 mm, or from about 15 mm to about 22 mm. The maximum diameter or width is typically measured at the widest portion of the pessary device substantially perpendicular to the longitudinal axis.

The pessary devices can have any suitable minimum diameter that is smaller than the maximum diameter, including, for example, a minimum diameter from about 40% to about 95% of the maximum diameter, from about 40% to about 90% of the maximum diameter, from about 40% to about 85% of the maximum diameter, from about 40% to about 80% of the maximum diameter, from about 45% to about 75% of the maximum diameter, or from about 50% to about 70% of the maximum diameter, such as, for example, about 45% of the maximum diameter, about 50% of the maximum diameter, about 55% of the maximum diameter, about 60% of the maximum diameter, about 65% of the maximum diameter, or about 70% of the maximum diameter.

The pessary devices can have a minimum diameter from about 4 mm to about 28 mm, about 5 mm to about 20 mm, about 8 mm to about 20 mm, from about 8 mm to about 18 mm, or from about 8 mm to about 15 mm, such as, for example, about 8 mm, about 8.5 mm, about 9 mm, about 9.5 mm, about 10 mm, about 10.5 mm, about 11 mm, about 11.5 mm, about 12 mm, about 12.5 mm, about 13 mm, about 13.5 mm, about 14 mm, about 14.5 mm, about 15 mm, about 15.5 mm, about 16 mm, about 16.5 mm, about 17 mm, about 17.5 mm, about 18 mm, about 18.5 mm, about 19 mm, about 19.5 mm, or about 20 mm, or any other suitable minimum diameter. The minimum diameter or width is typically measured at the narrowest portion of the pessary device substantially perpendicular to the longitudinal axis.

The maximum diameter and the minimum diameter can be separated by any suitable distance, such as, for example, by about 5 mm, about 10 mm, about 15 mm, about 20 mm, about 25 mm, about 30 mm, about 35 mm, about 40 mm, about 45 mm, about 50 mm, or any other suitable distance.

The pessary devices can have any suitable length, such as, for example, a length from about 35 mm to about 60 mm, about 40 mm to about 55 mm, or about 40 mm to about 50 mm, such as, for example, a length about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, or about 50 mm. The length is typically measured substantially parallel to the longitudinal axis of the pessary device.

Generally, the pessary device can have a weight of less than about 10 grams, less than about 9 grams, less than about 8 grams, less than about 7 grams, less than about 6 grams, less than about 5 grams, less than about 4 grams, less than about 3 grams, less than about 2 grams, or less than about 1 gram, including for example, a weight of from about 1 gram to about 7 grams, or from about 2 grams to about 6 grams, or from about 3 grams to about 5 grams.

Pessary devices can be fabricated using any suitable materials and methods. For example, pessaries can be formed from polymeric materials, such as, for example, polycarbonate, polyester, polyethylene, polyacrylamide, polyformaldehyde, polymethylmethacrylate, polypropylene, polytetrafluoroethylene, polytrifluorochlorethylene, polyvinylchloride, polyurethane, nylon, silicone, or mixtures or blends thereof, or metallic materials. In certain embodiments, the pessary devices are not formed from absorbent material such as, for example, fibrous material or absorbent foam.

Pessary devices can be formed in any suitable manner, such as, for example, using injection molding, blow molding, or other suitable methods of forming the pessary device. Pessary devices can be assembled by snapfitting two or more pieces together.

The pessary device must have one or more protuberances inside the hollow interior. The pessary device can have a plurality of protuberances. Protuberances can be integral or non-integral to the pessary device. Non-integral protuberances can be attached to the inner walls of the pessary device by any means commonly known to one of ordinary skill in the art including, such as, for example, adhesives and/or heat. Protuberances can be in the shape of a nub, a hook, a disc, a rod, triangle, pyramid, and/or any volumetric shape. The one or more protuberances can be used to anchor a withdrawal member. The one or more protuberances can provide structural support to the pessary device.

A protuberance can be used to cross an external opening to the pessary device. A protuberance can be used to connect one side of the hollow interior to the opposite side of the hollow interior crossing the longitudinal axis. One or more protuberances can form a bridge crossing the longitudinal axis. Two or more protuberances can meet at the longitudinal axis. Two or more protuberances can meet at a point between the longitudinal axis and the inner wall along the transverse axis. Protuberances can be located at different points along the longitudinal axis.

Two or more protuberances can meet and interlock within the hollow interior. Protuberances can interlock via any suitable method, such as, for example, ball and socket, lock and key, friction, and/or hooking parts. Two or more protuberances can be symmetrical to each other within the hollow interior along one or both of the longitudinal and/or transverse axis.

Protuberances can be made from polymeric materials, such as, for example, polycarbonate, polyester, polyethylene, polyacrylamide, polyformaldehyde, polymethylmethacrylate, polypropylene, polytetrafluoroethylene, polytrifluorochlorethylene, polyvinylchloride, polyurethane, nylon, silicone, or mixtures or blends thereof, or metallic materials. Protuberances can be made from a material that is provides more resistance to force than the material used to fabricate the pessary device.

The pessary device having one or more protuberances can be made by injection molding the entire pessary device. The one or more protuberances can be injection molded and attached to the pessary device. The pessary device having one or more protuberances can be made by injection molding one or more parts of the pessary device that snapfit with one or more injection molded parts of the pessary device to form a pessary device. For example, the pessary device can be made from a first injection molded part that snapfits with a second injection molded part. The first injection molded part and/or the second injection molded part can have a protuberance that interlocks with a protuberance in the first injection molded part and/or second injection molded part within the hollow interior. The first injection molded part and the second injection molded part can mirror each other.

The pessary device can be covered by an overwrap. The overwrap can be non-absorbent or absorbent and can include any suitable material, such as, for example, a fibrous nonwoven material comprising natural, synthetic, or a blend of natural and synthetic fibers. Suitable synthetic fibers can include, e.g., fibers such as polyester, polyolefin, nylon, polypropylene, polyethylene, polyacrylic, cellulose acetate, polyhydroxyalkanoates, aliphatic ester polycondensates, bicomponent fibers and/or mixtures thereof. Natural fibers can include, e.g., rayon and those commonly known to be non-synthetic and of natural origin such as cotton. The fibers can have any suitable cross-sectional shape, such as, e.g., round, tri-lobal, multi-lobal, delta, hollow, ribbon-shaped, and/or any other suitable shape, or mixtures thereof. Fibers with any suitable diameter can be used, such as, e.g., from about 0.5 to about 50 microns, such as, e.g., from about 1 to about 30 microns, such as, e.g., from about 10 to about 25 microns. Fiber diameter can be determined using any suitable means; however, for non-round fibers, diameter can typically be determined by reference to the diameter of a fiber with the same cross-sectional area as the non-round fiber.

The overwrap can be made by any number of suitable techniques and can have any suitable basis weight. Suitable techniques include, for example, carding, meltblowing, spunbonding, spunlacing, air laying, and the like. For example, the overwrap can be formed using bonding methods, such as, e.g., thermal, ultrasonic, resin, through-air bonding, hydroentangling, and/or needling. The basis weight of the overwrap can be any suitable weight, such as, e.g., from about 10 to about 60 grams per square meter (gsm), such as, e.g., from about 15 to about 30 gsm. In addition, the overwrap can be hydrophilic or hydrophobic.

The overwrap can be joined to the pessary device by any variety of means. The overwrap can be joined to itself or to the pessary device. For example, one portion of overwrap can be joined to an opposed portion of the overwrap or to the pessary device using any suitable adhesive or heat pressure bonding means. Such adhesive can extend continuously along the length of attachment or it can be applied in a non-continuous fashion at discrete intervals. Heat bonding includes thermally bonding, fusion bonding, or any other suitable means for joining such materials.

The pessary device can include a withdrawal member that can comprise any suitable material, including for example, cotton, cellulose, rayon, polyolefins such as, for example, polyethylene or polypropylene, nylon, silk, polytetrafluoroethylene, wax, or any other suitable materials.

The withdrawal member can be formed by any suitable formation method and in any suitable configuration, such as, e.g., one or more cords, strings, finger covers, ribbons, an extension of a material of the device, or combinations thereof.

The withdrawal member can be anchored to a protuberance inside the pessary device hollow interior. The withdrawal member can be wrapped around a protuberance inside the pessary device hollow structure. The withdrawal member can be held by two or more protuberances by friction, entanglement, clamping, and/or interference. The withdrawal member can cross through an enclosed space formed by two or more protuberances.

The pessary device can be inserted using an applicator that can include an insertion member and a plunger. The insertion member can have an insertion end and a withdrawal end opposite the insertion end. The insertion member also can include a barrel region adapted to contain the pessary device, and a grip region that can, in certain embodiments, be an indentation region provided opposite the insertion end, such as, e.g., proximal to the withdrawal end.

The insertion member and/or plunger can be constructed from any suitable material. Suitable materials include, for example, paper, paperboard, cardboard, cellulose, such as, e.g., molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, poly hydroxyalkanoate, ethylene vinyl acetate, polyurethane, silicone, derivatives thereof, copolymers thereof, mixtures thereof, or any suitable smooth plastic material. Examples of suitable materials are disclosed in, e.g., U.S. Pat. Nos. 5,346,468 and 5,558,631. Additives can be included in the material to alter or enhance certain material properties. Suitable additives include, for example, mold release agents, slip agents, surface energy modifiers, pearlescent agents, and/or any other suitable additives. The insertion member also or alternatively can be coated with a substance to give it a high slip characteristic, such as, e.g., with wax, polyethylene, a combination of wax and polyethylene, cellophane, clay, mica, and other lubricants that can facilitate comfortable insertion. Alternatively, or in addition, the insertion member can include a textured surface. Texture can be provided in any suitable manner, such as, e.g., by designing texture into or adding texture to the insertion member.

The insertion member can include a grip region, such as, for example, an indentation region. The grip region can have a plurality of three-dimensional surface elements, such as, e.g., projections, rings, ridges, ribs, embossments, depressions, grooves, and/or other gripping structures. The three-dimensional surface elements can be provided in any suitable manner, such as, e.g., by the addition of material, and/or by impressing, such as, e.g., by embossing, or compressing the surfaces. For example, the indentation region can include one or more flattened sides and/or one or more spaces for a decorative marking or a character, such as, e.g., an embossed and/or printed marking or character. In addition, or alternatively, the surfaces of the indentation region can include a material that can provide a frictional resistance for the user's fingers during the insertion of the applicator into the body. Suitable materials that can provide friction include, for example, abrasive materials, high wet coefficient of friction materials, pressure sensitive adhesives, or any combinations thereof.

The pessary device can be used daily. For example, in certain embodiments, a user can insert the pessary device, wear the pessary device for a suitable wear time, such as, for example, up to 4 hours, up to 5 hours, up to 6 hours, up to 7 hours, up to 8 hours, up to 9 hours, up to 10 hours, up to 11 hours, or up to 12 hours, or more, remove the pessary device, dispose of the pessary device, and insert a new pessary device.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A pessary device having a top, a base, a length, a longitudinal axis, a sidewall that extends between the top and the base, and a hollow interior, wherein the top, the base, and the sidewall form an outer periphery defining a total area of the device, wherein the hollow interior is substantially enclosed by the top, the base, and the sidewall, wherein the hollow interior comprises a protuberance that anchors a withdrawal member, and wherein the pessary device is non-expandable.

2. The pessary device of claim 1, wherein the protuberance is integral to an inner wall of the pessary device.

3. The pessary device of claim 1, wherein the protuberance is non-integral to an inner wall of the pessary device.

4. The pessary device of claim 1, wherein the pessary device further comprises a first portion and a second portion that snap fit together along the longitudinal axis.

5. The pessary device of claim 4, wherein the first portion and the second portion each comprise a protuberance.

6. The pessary device of claim 5, wherein the protuberance of the first portion and the protuberance of the second portion interlock within the hollow interior.

7. The pessary device of claim 1, wherein the protuberance is made of a material selected from the group consisting of polycarbonate, polyester, polyethylene, polyacrylamide, polyformaldehyde, polymethylmethacrylate, polypropylene, polytetrafluoroethylene, polytrifluorochlorethylene, polyvinylchloride, polyurethane, nylon, silicone, or mixtures or blends thereof, metallic materials, and/or combinations thereof.

8. The pessary device of claim 1, wherein the pessary device comprises of a plurality of protuberances and wherein the plurality of protuberances do not contact each other.

9. The pessary device of claim 1, wherein the pessary device comprises two or more protuberances and wherein the withdrawal member is held by the two or more protuberances.

10. The pessary device of claim 1, wherein the pessary device comprises two or more protuberances, wherein the two or more protuberances are in contact forming an enclosed space, and wherein the withdrawal member crosses through the enclosed space.

11. A pessary device having a top, a base, a length, a longitudinal axis, a sidewall that extends between the top and the base, and a hollow interior, wherein the top, the base, and the sidewall form an outer periphery defining a total area of the device, wherein the hollow interior is substantially enclosed by the top, the base, and the sidewall, wherein the pessary device is non-expandable, wherein the hollow interior comprises a plurality of protuberances that provide structural support within the pessary device.

12. The pessary device of claim 11, wherein the plurality of protuberances are integral to an inner wall of the pessary device.

13. The pessary device of claim 11, wherein the plurality of protuberance are non-integral to an inner wall of the pessary device.

14. The pessary device of claim 11, wherein the pessary device further comprises a first portion and a second portion that snap fit together along the longitudinal axis.

15. The pessary device of claim 14, wherein the first portion and the second portion each comprise a protuberance.

16. The pessary device of claim 15, wherein the protuberance of the first portion and the protuberance of the second portion interlock within the hollow interior.

17. The pessary device of claim 11, wherein the plurality of protuberances anchor a withdrawal member to the pessary device.

18. The pessary device of claim 11, wherein the plurality of protuberances are made of a material selected from the group consisting of polycarbonate, polyester, polyethylene, polyacrylamide, polyformaldehyde, polymethylmethacrylate, polypropylene, polytetrafluoroethylene, polytrifluorochlorethylene, polyvinylchloride, polyurethane, nylon, silicone, or mixtures or blends thereof, metallic materials, and/or combinations thereof.

19. The pessary device of claim 11, wherein the plurality of protuberances do not contact each other.

20. A pessary device having a top, a base, a length, a longitudinal axis, and a hollow interior, wherein the pessary device is non-expandable, wherein the hollow interior comprises two or more protuberances and a withdrawal member, wherein the two or more protuberances interlock by friction, and wherein the withdrawal member is held between the two or more protuberances.

* * * * *